(12) United States Patent
Abraham et al.

(10) Patent No.: US 9,937,133 B2
(45) Date of Patent: Apr. 10, 2018

(54) TREATMENT OF FIBROSIS

(71) Applicant: UCL BUSINESS PLC, London (GB)

(72) Inventors: David Abraham, London (GB); Virginia Calder, London (GB); Sarah Dale, London (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 15/307,155

(22) PCT Filed: May 1, 2015

(86) PCT No.: PCT/GB2015/051292
§ 371 (c)(1),
(2) Date: Oct. 27, 2016

(87) PCT Pub. No.: WO2015/166277
PCT Pub. Date: Nov. 5, 2015

(65) Prior Publication Data
US 2017/0042838 A1 Feb. 16, 2017

(30) Foreign Application Priority Data
May 2, 2014 (GB) .................................. 1407806.7

(51) Int. Cl.
| | | |
|---|---|---|
| A61K 31/145 | (2006.01) | |
| A61K 31/136 | (2006.01) | |
| A61K 8/41 | (2006.01) | |
| A61K 8/46 | (2006.01) | |
| A61K 9/00 | (2006.01) | |
| A61Q 19/00 | (2006.01) | |

(52) U.S. Cl.
CPC ............ *A61K 31/145* (2013.01); *A61K 8/411* (2013.01); *A61K 8/46* (2013.01); *A61K 9/0048* (2013.01); *A61K 31/136* (2013.01); *A61Q 19/00* (2013.01)

(58) Field of Classification Search
CPC ............................ A61K 31/145; A61K 31/136
See application file for complete search history.

(56) References Cited

FOREIGN PATENT DOCUMENTS

| CN | 103301097 | 11/2008 |
|---|---|---|
| CN | 101310713 | 9/2013 |
| WO | 1999034784 | 7/1999 |

OTHER PUBLICATIONS

Saw et al. (The American Journal of Pathology, vol. 178, No. 1, Jan. 2011, p. 187-197).*
Dart et al., "Ocular scarring and blindness: Studies on Mucous Membrane Pemphigoid", poster presentation at neeting "Flarre Consortium Presents: A Focus on Fibrosis", Feb. 25, 2014; 1 page.*
Dale, "Aldehyde dehydrogenase as a novel and potential therapy for conjunctival fibrosis", UCL Doctoral thesis, May 2014, 180 pages.*
Chen et al. (2012) "Puerarin prevents isoprenaline-induced myocardial fibrosis in mice by reduction of myocardial TGF-β1 expression", Journal of Nutritional Biochemistry 23; pp. 1080-1085.
Dale et al., "A novel contribution for dendritic cells in fibrosis pathobiology as revealed in a mouse model of severe ocular allergy", ARVO 2014 Annual Meeting Abstracts, available online Mar. 13, 2014.
Dale et al. (2014) "Aldehyde dehydrogenase as a novel and potential therapy for conjunctival fibrosis", Doctoral thesis extract, http://discovery.ucl.ac.uk/1433170; 4 pages.
Dart et al., "Ocular scarring and blindness: Studies on Mucous Membrane Pemphigoid", poster presentation at meeting "Flarre Consortium Presents: A Focus on Fibrosis", Feb. 25, 2014; 1 page.
Herrick et al. (1994) "A controlled trial of the effect of topical glyceryl trinitrate on skin blood flow and skin elasticity in scleroderma", Annals of the Rheumatic Diseases, 53(3), pp. 212.
Kanai et al., (2012) "Effects of Instillation of Eyedrops Containing Disulfiram and Hydroxypropyl-β-Cyclodextrin Inclusion Complex on Endotoxin-Induced Uveitis in Rats", Current Eye Research 37(2), 124-131.
Koppaka et al. (2012) "Aldehyde Dehydrogenase Inhibitors: a Comprehensive Review of the Pharmacology, Mechanism of Action, Substrate Specificity, and Clinical Application", Pharmacol Rev 64(3): pp. 520-539.
Nagai et al., "Effect of Eye Drops Containing Disulfiram and Low-Substituted Methylcellulose in Reducing Intraocular Pressure in Rabbit Models", Current Eye Search, Early Online, pp. 1-11, Oct. 20, 1014.
Nagai et al. (2012) "Pharmacokinetic and Pharmacodynamic Evaluation of the Anti-cataract Effect of Eye Drops containing Disulfiram and Low-Substituted Methylcellulose Using ICR/f Rats as a Hereditary Cataract Model", Biol. Pharm. Bull. 35(2); pp. 239-245.
Poorasjedi-Meibod et al., "Anti-scarring Properties of Different Tryptophan Derivatives", PLOS ONE, 9(3), e91955, (Mar. 2014).
Shimamura et al. (2006) "Effect of Intermittent Administration of Sustained Release Isosorbide Dintrate (sr-ISDN) in Rats with Pressure-Overload Heart", Journal of Veterinary Medicine 68(3); pp. 213-217.
Zhang et al. (2006) "Reversal of chemical-induced liver fibrosis in Wistar rats by puerarin", Journal of Nutritional Biochemistry 17; pp. 485-491.

(Continued)

*Primary Examiner* — Robert Havlin
(74) *Attorney, Agent, or Firm* — Michael B. Rubin; Bozicevic, Field & Francis LLP (57) ABSTRACT

The present invention relates an aldehyde dehydrogenase inhibitor for use in the treatment or prevention of fibrosis.

4 Claims, 5 Drawing Sheets

(56) References Cited

OTHER PUBLICATIONS

Search Report issued by UK IPO on British priority application GB 1407806.7, dated Dec. 16, 2014.
International Search Report and Written Opinion dated Sep. 16, 2015 for PCT/GB2015/051292.

* cited by examiner

TREATMENT OF FIBROSIS

FIELD OF THE INVENTION

The present invention relates to the treatment and/or prevention of fibrosis.

BACKGROUND TO THE INVENTION

Fibrosis is the formation of excess fibrous connective tissue in an organ or tissue in response to an injury and/or inflammation. Fibrosis in response to an injury is also called scarring. Fibrosis may also arise due to pathological states, such as mucous membrane pemphigoid (MMP), pulmonary fibrosis and scleroderma.

Pulmonary fibrosis and scleroderma are leading causes of mortality. Mucous membrane pemphigoid (MMP) is a systemic autoimmune disease characterized by inflammation and variable blistering and scarring of one or more of the mucous membranes and the skin. MMP affecting the conjunctiva is known as ocular MMP (OcMMP) and can rapidly cause blindness in patients.

There are at present no approved therapeutic treatments specifically for fibrosis, and current immunosuppressive or anti-inflammatory therapies are generally ineffective. There is therefore a need for new drugs which can reduce or prevent the formation of excess fibrous connective tissue, and thereby treat diseases involving fibrosis, such as mucous membrane pemphigoid, pulmonary fibrosis and scleroderma. One particular need is for drugs that can be used to treat or prevent fibrosis in the eye, for example OcMMP.

SUMMARY OF THE INVENTION

The present inventors surprisingly found when investigating gene expression in OcMMP fibroblasts that aldehyde dehydrogenase 1 family member A3 (ALDH1A3) is up regulated in OcMMP. Elevated expression of ALDH1A3 was then confirmed by quantitative polymerase chain reaction (qPCR) and protein levels were assessed by western blot. In view of this surprising finding, aldehyde dehydrogenase inhibitors were added to OcMMP fibroblasts, which resulted in the restoration of phenotype and function to control cell levels. These results suggest that inhibition of aldehyde dehydrogenase using aldehyde dehydrogenase inhibitors should provide an effective therapy for treating or preventing fibrosis.

Accordingly, the present invention provides an aldehyde dehydrogenase inhibitor for use in the treatment or prevention of fibrosis.

The invention further provides use of an aldehyde dehydrogenase inhibitor in the manufacture of a medicament for treating or preventing fibrosis.

The invention further provides a method for treating or preventing fibrosis in a patient in need thereof, the method comprising adminstering to said patient an aldehyde dehydrogenase inhibitor.

The invention further provides a cosmetic method for treating scarring in response to an injury in a subject, the method comprising administering an aldehyde dehydrogenase inhibitor to the subject.

BRIEF DESCRIPTION OF THE FIGURES

FIGS. 1A-1D show the results from a genome wide microarray carried out as described in Example 1.

FIGS. 2A-2E show the results from investigations into differential matrix production in OcMMP as described in Example 2.

FIGS. 3A-3E show the results from investigations into the ability of fibroblasts to organise matrix through matrix contraction as described in Example 3.

FIGS. 4A-4E show the results of investigations into the proliferative capacity of F-PemI, F-PemU and F-C fibroblasts as described in Example 4.

DETAILED DESCRIPTION OF THE INVENTION

The present invention relates to the treatment and/or prevention of fibrosis using aldehyde dehydrogenase inhibitors.

Aldehyde Dehydrogenase Inhibitors

Aldehyde dehydrogenases are a group of enzymes that catalyse the oxidation (ie. dehydrogenation) of aldehydes to carboxylic acids. The Enzyme Commission (EC) number for aldehyde dehydrogenase (ALDH) is EC 1.2.1.3.

Nineteen genes coding for aldehyde dehydrogenases have been identified within the human genome. These are ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH8A1, ALDH9A1, ALDH16A1 and ALDH18A1.

An aldehyde dehydrogenase inhibitor is a compound that is capable of inhibiting the activity of one or more aldehyde dehydrogenase enzymes. Typically, the aldehyde dehydrogenase inhibitor is capable of inhibiting ALDH1A3. In some embodiments, it may be preferred that the aldehyde dehydrogenase inhibitor is selective for one specific aldehyde dehydrogenase enzyme, for example ALDH1A3.

Typically, an aldehyde dehydrogenase inhibitor is a compound with an $IC_{50}$ for the aldehyde dehydrogenase enzyme of less than 100 nM, preferably 10 to 100 nM, for example less than 90 nM, less than 80 nM, less than 70 nM, less than 60 nM or less than 50 nM.

Various methods and assays are known to those of skill in the art for measuring aldehyde dehydrogenase activity and one suitable method is described below in the Examples. Commercially available test kits are also available for measuring aldehyde dehydrogenase activity.

The ability of a compound to act as an aldehyde dehydrogenase inhibitor can be determined by comparing the activity of aldehyde dehydrogenase in the presence and absence of the test compound. Aldehyde dehydrogenase activity is reduced in the presence of a test compound which is an aldehyde dehydrogenase inhibitor. The $IC_{50}$ value for the test compound can be determined by, for example, measuring aldehyde dehydrogenase activity at various different concentrations of the test compound and constructing a dose-response curve.

A skilled person can readily identify suitable aldehyde dehydrogenase inhibitor for use in the invention. For example, the compounds described in *Pharmacol Rev* 64:520-539, 2012, Koppaka et al can be used.

Thus, the aldehyde dehydrogenase inhibitor is typically tetraethylthioperoxydicarbonic diamide (disulfiram), 4-(diethylamino)benzaldehyde (DEAB), 4-(N,N-dipropylamino) benzaldehyde, 4-amino-4-methyl-2-pentyne-1-al (AMPAL), 2-methyl-5-(methylsulfanyl)-5-oxopentan-2-aminium, 4-methyl-1-(methylsulfanyl)-4-(2,2,5,5-tetramethylpyrrolidin-1-yl) pent-2-yn-1-one), 4-(dimethylamino)-4-methyl-1-(methylsulfanyl)pent-2-yn-1-one, methyl [1-[(butylamino) carbonyl]-1H-benzimidazol-2-yl]carbamate (benomyl), trichloroacetaldehyde monohydrate (chloral), chlorpropamide, tolbutamide, (benzoyloxy)[(4-chlorophenyl)sulfonyl]carbamic acid 1,1-dimethylethyl ester, 4-chloro-N-ethyl-N-[(propylamino)carbonyl]benzenesulfonamide, 3,7-dimethyl-2,6-octadienal (citral), N-(1-Hydroxycyclopropyl)-L-glutamine (coprine), calcium 2-hydroxypropane-1,2,3-tricarboxylate, methylcyanamide (temposil), daidzin, daidzein, puerarin, gossypol, 3-hydroxykynurenine, 3-hydroxyanthranilic acid, kynurenic acid, indol-3-ylpyruvic acid, molinate, pebulate, vernolate, butylate, triallate, cycloate, nitroglycerin, isosorbide dinitrate or N-benzyl-N-methylprop-2-yn-1-amine (pargyline), or a pharmaceutically acceptable salt or ester of any thereof.

Preferably, the aldehyde dehydrogenase inhibitor is disulfiram or DEAB, more preferably disulfiram.

The pharmaceutically acceptable salt is typically a salt with a pharmaceutically acceptable acid and thus includes those formed with an inorganic acid such as hydrochloric or sulphuric acid or an organic acid such as citric, tartaric, malic, maleic, mandelic, fumaric or methanesulphonic acid.

The pharmaceutically acceptable ester is typically a $C_{1-6}$ alkyl ester, preferably a $C_{1-4}$ alkyl ester. The ester may for example therefore be the methyl, ethyl, propyl, isopropyl, butyl, isobutyl or tert-butyl ester.

A further preferred type of aldehyde dehydrogenase inhibitor is an antibody that specifically binds to one or more aldehyde dehydrogenases, in particular one or more of the 19 human aldehyde dehydrogenase identified above, especially ALDH1A3. The term "antibody" as referred to herein includes whole antibodies and any antigen binding fragment (i.e., "antigen-binding portion") or single chains thereof.

An antibody of the invention may be a monoclonal antibody or a polyclonal antibody.

The term "antigen-binding portion" of an antibody refers to one or more fragments of an antibody that retain the ability to specifically bind to an antigen. Examples of binding fragments encompassed within the term "antigen-binding portion" of an antibody include a Fab fragment, a $F(ab')_2$ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody.

An antibody of the invention may be a chimeric antibody, a CDR-grafted antibody, a nanobody, a human or humanised antibody or an antigen binding portion of any thereof.

In one preferred embodiment, the antibody of the invention is a human antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. Such a human antibody may be a human monoclonal antibody. Binding affinity may be quantified by determining the dissociation constant (Kd) for an antibody and its target. Similarly, the specificity of binding of an antibody to its target may be defined in terms of the comparative dissociation constants (Kd) of the antibody for its target as compared to the dissociation constant with respect to the antibody and another, non-target molecule.

Antibodies of the invention will desirably bind to aldehyde dehydrogenase with high affinity, preferably in the picomolar range, e.g. with an affinity constant ($K_D$) of 10 nM or less, 1 nM or less, 500 pM or less or 100 pM or less, measured by surface plasmon resonance or any other suitable technique.

Specific binding may be assessed with reference to binding of the antibody to a molecule that is not the target. This comparison may be made by comparing the ability of an antibody to bind to the target and to another molecule. This comparison may be made as described above in an assessment of Kd or Ki. The other molecule used in such a comparison may be any molecule that is not the target molecule. For example, the Kd of the antibody for the target aldehyde dehydrogenase compared to that of the non-target molecule may be greater than 100-fold, 1,000-fold, greater than 10,000-fold, greater than 100,000-fold or greater than 1,000,000-fold lower than the affinity for the non-target molecule.

Depending on which epitope it binds, an antibody may specifically bind to all aldehyde dehyrogenases, multiple aldehyde dehyrogenases or selectively to one or a few aldehyde dehyrogenases, such as ALDH1A3. In cases where the antibody is selective for a particular aldehyde dehydrogenase over other aldehyde dehyrogenases In the case of a selective antibody, selectivity will typically be greater than 500 fold, greater than 750 fold or greater than 1000 fold for the target aldehyde dehydrogenase(s), such as ALDH1A3 compared to a non-target aldehyde dehydrogenase.

Antibodies of the invention can be tested for binding to aldehyde dehydrogenase inhibitor by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example by flow cytometry.

Once a suitable antibody has been identified and selected, the amino acid sequence of the antibody may be identified by methods known in the art. The genes encoding the antibody can be cloned, for example using degenerate primers. The antibody may be recombinantly produced by routine methods.

Therapeutic Indications

The present invention is concerned with the treatment and/or prevention of fibrosis in a subject, particularly fibrosis in the eye. Typically, the subject is a human or non-human animal. The term "non-human animal" includes all vertebrates, e.g., mammals and non-mammals, including non-human primates such as monkeys and apes, sheep, dogs, cats, horses, cows, pigs, chickens, amphibians, reptiles, etc. Administration to humans is preferred.

Fibrosis is the formation of excess fibrous connective tissue in an organ or tissue in response to an injury and/or inflammation.

Fibrosis in response to an injury is also called scarring. In some embodiments, therefore, the fibrosis treated in the present invention is scarring. Such scarring may have any cause, e.g. surgery or accident. For example, the fibrosis treated in the present invention may be scarring following glaucoma filtration surgery or corneal graft.

Fibrosis may also arise due to a pathological state. Examples of pathological states where formation of excess fibrous connective arises include mucous membrane pemphigoid (MMP), particularly ocular mucous membrane pemphigoid (OcMMP), pulmonary fibrosis, scleroderma, idiopathic pulmonary fibrosis, pulmonary and peripheral vascular disease, cystic fibrosis, cirrhosis, liver fibrosis, endomyocardial fibrosis, myocardial infarction, atrial fibrosis, cardial fibrosis, mediastinal fibrosis, myelofibrosis, atherosclerosis, retroperitoneal fibrosis, progressive massive fibrosis, nephrogenic systemic fibrosis, Crohn's disease, keloids, arthrofibrosis, Peyronie's disease, Dupuytren's contracture, adhesive capsulitis or trachoma.

Preferably the fibrosis is ocular mucous membrane pemphigoid (OcMMP), pulmonary fibrosis or scleroderma, more preferably ocular mucous membrane pemphigoid (OcMMP). Preferably the fibrosis is fibrosis in the eye. For the avoidance of doubt, and as is evident from the fact that OcMMP is susceptible to treatment according to the present invention, the eye as referred to herein includes not only the eye ball itself, but also the conjunctiva and eye lids.

When the fibrosis is ocular mucous membrane pemphigoid (OcMMP), it is preferred that the aldehyde dehydrogenase inhibitor is an ALDH1A3 inhibitor, more preferably a selective ALDH1A3 inhibitor.

Cosmetic Indications

In some cases, treatment or prevention of scarring may be carried out for non-therapeutic and/or cosmetic purposes. Thus, the present invention also relates to a cosmetic method for treating scarring in response to an injury in a subject, the method comprising administering an aldehyde dehydrogenase inhibitor to the subject. The subject is typically human. Administration is typically topical, preferably in the form or a cosmetic composition such as a cream, lotion or ointment.

Pharmaceutical Compositions and Route of Administration

The aldehyde dehydrogenase inhibitor may be administered as a pharmaceutical composition by any suitable route, depending on the nature of the fibrosis to be treated. For example, administration may be oral (as syrups, tablets, capsules, lozenges, controlled-release preparations, fast-dissolving preparations, etc), topical (as creams, ointments, lotions, nasal sprays or aerosols, etc), by injection (subcutaneous, intradermal, intramuscular, intravenous, etc), or by inhalation (as a dry powder, a solution, a dispersion, etc).

Topical and inhaled administration are preferred, with topical administration most preferred, since the systemic side effects that may arise with oral administration or injection do not tend to arise with topical or inhaled administration. Nevertheless, the preferred route of administration will depend upon the specific form of fibrosis to be treated, and in particular the location of the formation of the excess fibrous connective tissue.

For example, if the fibrosis occurs in the eye, such as with ocular mucous membrane pemphigoid, then the aldehyde dehydrogenase inhibitor is preferably administered topically, for example as eye drops or as an ointment. Oral administration, for example by tablet, is however also possible.

Similar, if the fibrosis occurs on the skin, such as with scleroderma, then the aldehyde dehydrogenase inhibitor is preferably administered topically, for example as a cream, lotion or ointment.

Alternatively, if the fibrosis occurs in the lungs, such as with pulmonary fibrosis, then the aldehyde dehydrogenase inhibitor is preferably administered by inhalation, for example as a dry powder (eg. from a dry power inhaler) or as a solution/suspension (eg. from a nebulizer or pressurized metered dose inhaler).

Pharmaceutical compositions comprising the aldehyde dehydrogenase inhibitor may be prepared any suitable method known to those of skill in the art. The pharmaceutical compositions typically comprises one or more pharmaceutically acceptable carriers.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be preferable to include isotonic agents, for example, sugars, polyalcohols such as mannitol, sorbitol, or sodium chloride in the composition.

Pharmaceutical compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients, such as an additional therapeutic or prophylactic agent intended, for example, for the treatment of the same condition or a different one, or for other purposes such as amelioration of side effects. For example, if the fibrosis is idiopathic pulmonary fibrosis, then a suitable additional therapeutic agent would be pirfenidone.

Dosages and Dosage Regimes

A suitable dosage of the aldehyde dehydrogenase inhibitor may be determined by a skilled medical practitioner. Typically the dosage of the aldehyde dehydrogenase inhibitor is 1 to 500 mg per day, preferably 10 to 250 mg per day, for example about 25 or about 50 mg per day.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. Thus, the dosage is typically an effective or therapeutically effective dosage.

The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Dosage regimens may be adjusted to provide the optimum desired response. For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the drugs in the patient and the duration of treatment desired.

Topical administration to the eye, typically to the ocular surface, is preferred, and administration may be in single or multiple doses. The dosage and frequency of administration will depend upon a variety of factors, such as those discussed above, and also the vehicle in which the aldehyde dehydrogenase inhibitor is delivered and/or the half-life of the aldehyde dehydrogenase inhibitor at the ocular surface. Typically, each dose of the aldehyde dehydrogenase inhibitor administered topically to the eye has a volume of 10 to 100 µL, for example about 50 µL. Typically, the concentration of aldehyde dehydrogenase inhibitor in the formulation administered topically to the eye is no more than 0.5% m/v (mass/volume), preferably 0.001 to 0.1% m/v. Thus, is preferred that each dose of the aldehyde dehydrogenase inhibitor administered topically to the eye has a volume of 10 to 100 µL, for example about 50 and contains the aldehyde dehydrogenase inhibitor at a concentration of no more than 0.5% m/v, preferably 0.001 to 0.1% m/v.

Further Aspects of the Present Invention

The following are further specific aspects of the present invention as described in the foregoing disclosure:

[1] An aldehyde dehydrogenase inhibitor for use in the treatment or prevention of fibrosis.

[2] The aldehyde dehydrogenase inhibitor for use according to [1], wherein the aldehyde dehydrogenase inhibitor is tetraethylthioperoxydicarbonic diamide (disulfiram) or 4-(diethylamino)benzaldehyde (DEAB).

[3] The aldehyde dehydrogenase inhibitor for use according to [2], wherein the aldehyde dehydrogenase inhibitor is disulfiram.

[4] The aldehyde dehydrogenase inhibitor for use according to any one of [1] to [3], wherein the fibrosis is mucous membrane pemphigoid (MMP), pulmonary fibrosis or scleroderma.

[5] The aldehyde dehydrogenase inhibitor for use according to [4], wherein the fibrosis is ocular mucous membrane pemphigoid (OcMMP).

[6] The aldehyde dehydrogenase inhibitor for use according to [5], wherein the aldehyde dehydrogenase inhibitor is administered topically to the eye.

[7] The aldehyde dehydrogenase inhibitor for use according to [4], wherein the fibrosis is pulmonary fibrosis.

[8] The aldehyde dehydrogenase inhibitor for use according to [7], wherein the aldehyde dehydrogenase inhibitor is administered by inhalation.

[9] The aldehyde dehydrogenase inhibitor for use according to [4], wherein the fibrosis is scleroderma.

[10] The aldehyde dehydrogenase inhibitor for use according to any one of [1] to [3], wherein the fibrosis is scarring in response to an injury.

[11] The aldehyde dehydrogenase inhibitor for use according to [9] or [10], wherein the aldehyde dehydrogenase inhibitor is administered topically to the skin.

[12] Use of an aldehyde dehydrogenase inhibitor as defined in any one of [1] to [3], in the manufacture of a medicament for treating or preventing fibrosis, wherein said fibrosis is as defined in any one of [1], [4], [5], [7], [9] or [10].

[13] A method for treating or preventing fibrosis in a patient in need thereof, the method comprising adminstering to said patient an aldehyde dehydrogenase inhibitor as defined in any one of [1] to [3], wherein said fibrosis is as defined in any one of claims [1], [4], [5], [7], [9] or [10].

[14] A cosmetic method for treating scarring in response to an injury in a subject, the method comprising administering an aldehyde dehydrogenase inhibitor as defined in any one of [1] to [3] to the subject.

The following Examples illustrate the invention.

EXAMPLES

Examples 1 to 5 describe experiments in which up regulation of ALDH1A3 in OcMMP was identified and aldehyde dehydrogenase inhibitors were found to restore the phenotype and function of OcMMP fibroblasts to that of healthy fibroblasts. In particular, Example 1 demonstrates that ALDH1A3 is up regulated in OcMMP. Examples 2 to 5 demonstrate that four measures of fibroblast health (ie. matrix production, matrix organization, proliferative capacity and alpha smooth muscle actin alignment) are all abnormal in OcMMP fibroblasts. However, these measures of fibroblast health can be returned to normal levels by administration of aldehyde dehydrogenase inhibitors.

The experimental protocols used in Examples 1 to 5 are set out below, together with an assay that can be used to assess aldehyde dehydrogenase activity and thereby determine whether a test compound is an aldehyde dehydrogenase inhibitor.

Example 6 describes mouse model in vivo studies in which an aldehyde dehydrogenase inhibitor was applied to mice in daily eye drops.

Example 1—ALDH1A3 is Up Regulated in OcMMP

Figures 1A, 1B, 1C:
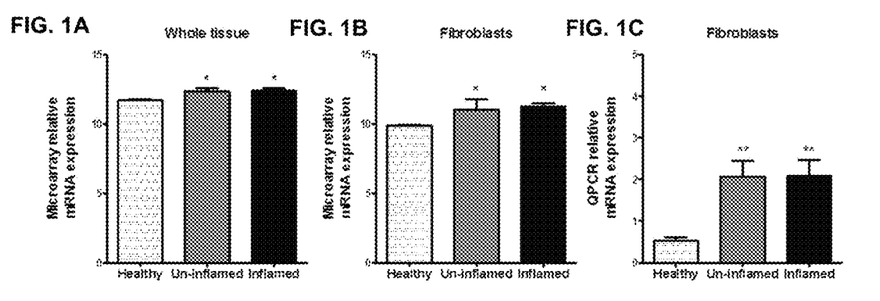
FIG. 1A shows the microarray results from OcMMP whole conjunctival tissue from patients with inflammation, from patients with no inflammation after treatment and from healthy patients.
FIG. 1B shows the microarray results from primary conjunctival fibroblasts explanted from these tissues.
FIG. 1C depicts Q-PCR results from fibroblasts explanted from these tissues and FIG. 1D shows the western blot analysis for fibroblasts explanted from these tissues. These results confirm increased expression of ALDH1A3 in OcMMP.
Figure 1D:
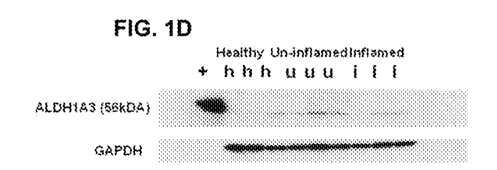

A genome wide microarray was carried out on OcMMP whole conjunctival tissue from patients with inflammation after treatment, from patients with no inflammation after treatment and from healthy patients, and with primary conjunctival fibroblasts explanted from these tissues. The results are depicted in FIGS. 1A and 1B. Q-PCR (see FIG. 1C) and western blot analysis (see FIG. 1D) confirmed increased expression of ALDH1A3.

Example 2—ALDH1A3 Exacerbates Matrix Production

Figure 2A:
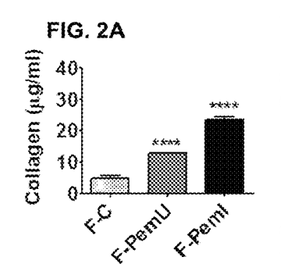
FIG. 2A shows that primary conjunctival fibroblasts explanted from conjunctival tissue samples from OcMMP patients with (F-PemI) and without (F-PemU) inflammation exhibited significantly higher collagen production compared to healthy (F-C) fibroblasts.
Figure 2B:
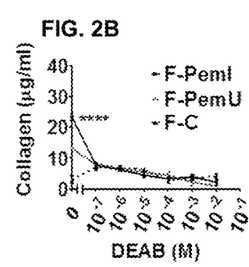
FIGS. 2B-2E shows the results from the addition of DEAB and disulfiram to fibroblasts, where "+" and "−" indicate the presence or absence of DEAB/disulfiram respectively. F-PemI and F-PemU fibroblast collagen production was brought down to control cell levels after only $10^{-7}$M DEAB and disulfiram addition.
Figure 2C:
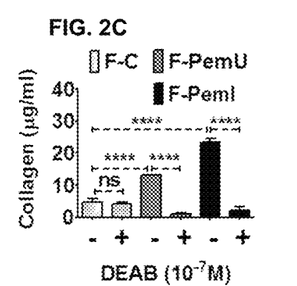
Figure 2D:
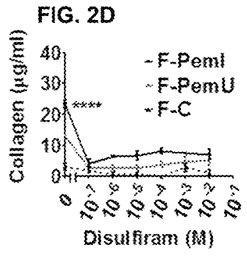
Figure 2E:
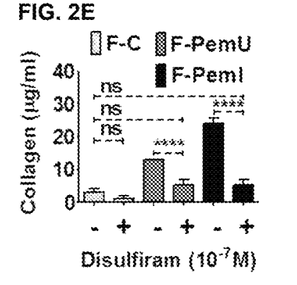

To investigate whether there was differential matrix production in OcMMP, primary conjunctival fibroblasts explanted from conjunctival tissue samples from OcMMP patients with (F-PemI) and without (F-PemU) and control (F-C) patients were analysed for their matrix production and secretion (see FIG. 2A). F-PemI and F-PemU fibroblasts exhibited significantly higher collagen production compared to F-C fibroblasts. The collagen production profiles of F-PemI and F-PemU fibroblasts did not significantly differ from one another.

To ascertain whether this enhanced collagen production was mediated by ALDH1A3, the collagen production profiles of F-PemI, F-PemU and F-C fibroblasts were assessed after ALDH inhibition with DEAB or disulfiram (see FIGS. 2B to 2E, where "+" and "−" indicate the presence or absence of DEAB/disulfiram respectively). Increasing concentrations of DEAB and disulfiram resulted in a dose dependent and significant decrease in F-PemI and F-PemU fibroblast collagen production. F-PemI and F-PemU fibroblast collagen production was brought down to control cell levels after only $10^{-7}$M DEAB and disulfiram addition.

Example 3—ALDH1A3 Impairs Matrix Organisation

Figure 3A:
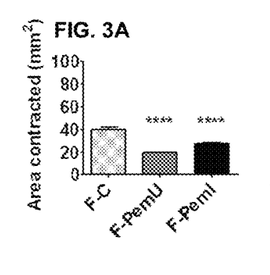
FIG. 3A shows that F-PemI and F-PemU fibroblasts showed a significantly decreased capacity to contract matrix in comparison to F-C fibroblasts.
Figure 3B:
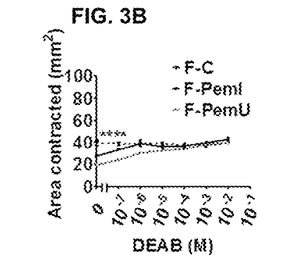
FIGS. 3B-3E show the results from addition of DEAB and disulfiram to fibroblasts, where "+" and "−" indicate the presence or absence of DEAB/disulfiram respectively. The lowest concentration of $10^{-7}$M DEAB and disulfiram addition resulted in F-PemI and F-PemU fibroblasts exhibiting control cell levels of contraction.
Figure 3C:
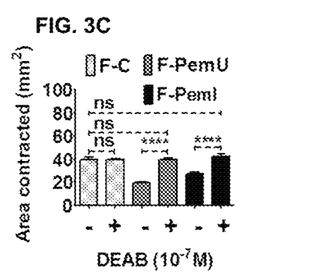
Figure 3D:
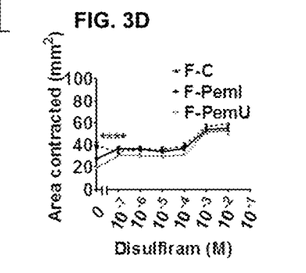
Figure 3E:
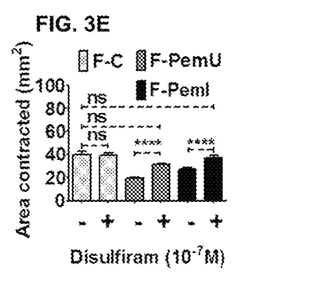

Next the ability of F-PemI and F-PemU fibroblasts to organise matrix through matrix contraction was investigated. F-PemI and F-PemU fibroblasts showed a significantly decreased capacity to contract matrix in comparison to F-C fibroblasts (see FIG. 3A). This diminished contractile profile was similar in F-PemI and F-PemU fibroblasts.

To find out whether ALDH1A3 was also contributing to this phenotypic contractility we looked at the contractile profiles of F-PemI, F-PemU and F-C fibroblasts after DEAB or disulfiram ALDH inhibition. Both DEAB and disulfiram addition increased the contractility of F-PemI and F-PemU fibroblasts in a dose dependent manner (see FIGS. 3B to 3E, where "+" and "−" indicate the presence or absence of DEAB/disulfiram respectively). The lowest concentration of $10^{-7}$M DEAB and disulfiram addition resulted in F-PemI and F-PemU fibroblasts exhibiting control cell levels of contraction. DEAB and disulfiram addition did not have any significant effects on the contractile profile of F-C fibroblasts.

Example 4—ALDH1A3 Exerts Anti-Proliferative Capacity

Figure 4A:
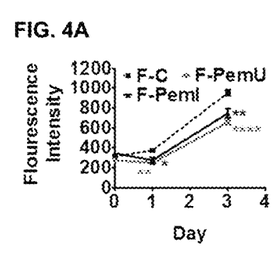
FIG. 4A shows that F-PemI and F-PemU fibroblasts exhibited significantly lower rates of proliferation than F-C fibroblasts.
Figure 4B:
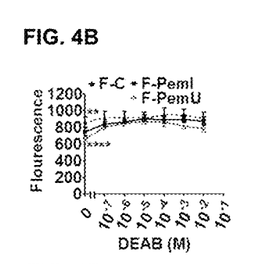
FIGS. 4B-4E show the results from addition of DEAB and disulfiram to fibroblasts, where "+" and "−" indicate the presence or absence of DEAB/disulfiram respectively. At the lowest concentration of $10^{-7}$M DEAB and disulfiram F-PemI and F-PemU fibroblasts proliferated at similar level to F-C fibroblasts.
Figure 4C:
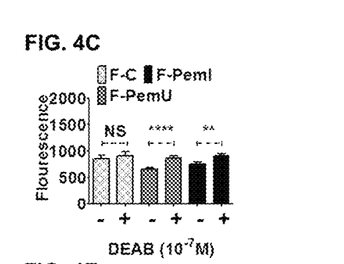
Figure 4D:
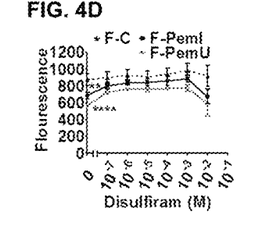
Figure 4E:
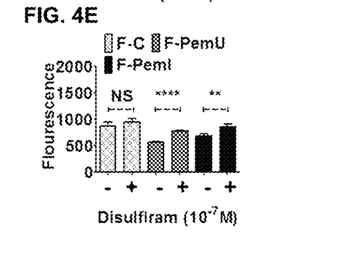

The proliferative capacity of F-PemI, F-PemU and F-C fibroblasts was also assessed. F-PemI and F-PemU fibroblasts exhibited significantly lower rates of proliferation than F-C fibroblasts. The proliferative capacities of F-PemI and F-PemU were similar (see FIG. 4A).

To find out whether ALDH1A3 also mediates this anti-proliferative phenotype we monitored the proliferation of F-PemI, F-PemU and F-C fibroblasts after addition of DEAB or disulfiram. DEAB and disulfiram inhibition of ALDH1A3 led to F-PemI and F-PemU fibroblasts proliferating at a significantly enhanced rate (see FIGS. 4B to 4E, where "+" and "−" indicate the presence or absence of DEAB/disulfiram respectively). At the lowest concentration of $10^{-7}$M DEAB and disulfiram F-PemI and F-PemU fibroblasts proliferated at similar level to F-C fibroblasts. F-C fibroblasts exhibited a similar proliferation profile before and after DEAB and disulfiram addition.

Example 5—ALDH1A3 Impairs Alpha Smooth Muscle Actin Alignment

Finally to have an indication of the differentiation capacity of F-PemI and F-PemU fibroblasts, their expression and alignment of alpha-smooth muscle actin under a stressed matrix was investigated. F-PemI and F-PemU lack the ability to align their alpha-smooth muscle actin into stress fibers when compared to F-C fibroblasts. The diminished alignment of alpha-smooth muscle actin was similar in both F-PemI and F-PemU fibroblasts.

To elucidate whether ALDH1A3 is contributing to this impaired alignment of alpha-smooth muscle actin in F-PemI and F-PemU fibroblasts, their alpha-smooth muscle actin alignment was imaged after being treated with DEAB and disulfiram. ALDH1A3 inhibition with DEAB and disulfiram markedly improved the alignment of alpha-smooth muscle actin in F-PemI and F-PemU fibroblasts.

Experimental Protocols

A—Microarray
(i) Illumina Technology

Gene microarray technology provides a method of simultaneously analysing expression levels of mRNA transcripts across the whole human genome. One such microarray technology is provided by Illumina. Here, total RNA samples are first reverse transcribed into cDNA, with which, rounds of transcription are completed with fluorescent labelled RNA. Resultant labelled cRNA that is transcribed is then hybridized to gene specific probes within the Illumina microarray gene chips. Ultimately, only labelled cRNA bound to a gene probe will remain fluorescent thus indicating expression levels of particular gene transcripts.

RNA samples extracted from whole conjunctival tissue and primary conjunctival fibroblasts from OcMMP patients and controls were analysed via this method. Simultaneously analysing whole conjunctival tissue and primary conjunctival fibroblasts allows a direct way of isolating genes that are differentially regulated in-vivo and in-vitro. This gives additional credibility for the in-vitro surrogate scarring models in that genes are maintaining their differential regulation due to potential disease mechanisms and not as an eventuality of continual culture.

Microarray experiments were performed using the HumanHT-12 v4 BeadChip. Genes with expression profiles showing all of the following 3 criteria were chosen, I. Expression showing P<0.05 significant difference compared to controls, II. Expression that was greater than 1.5 fold compared to control, III. Greater than 1.5 fold expression in both whole tissue and fibroblasts when compared to controls.

(ii) Isolation of Total RNA

All conjunctival biopsies were taken from superior bulbar conjunctiva. Once a conjunctival biopsy was taken from a patient, it was put into an 1.5 ml RNA free micro centrifuge tube (Applied Biosystems, California USA) containing 500 µl of RNA later (Qiagen, Hilden GER) and stored at 4° C. overnight, then frozen at −80° C. The conjunctival tissue samples were placed into a Wheaton glass dounce, macerated through 15 strokes of the glass dounce on ice and further homogenised through gentle pipetting with a 19G needle (Fisher, Leicestershire UK).

The resultant homogenate was then subjected to the RNA isolation protocol as per manufacturer's instruction with a Qiagen RNeasy kit (Qiagen, Hilden GER). Total RNA was extracted from conjunctival tissue of 12 OcMMP patients and 5 age-matched controls (PemI, n=6; PemU, n=6; C, n=5) and from primary conjunctival fibroblasts from 12 OcMMP patients and 4 controls (F-PemI, n=6; F-PemU, n=6; F-C, n=4).

(iii) RNA Quality Control

RNA concentration and purity were analysed using the nanodrop (Thermo Scientific, Fisher, Leicestershire UK). The nanodrop is a spectrophotometer measuring the UV absorbance of nucleic acids. RNA gives a maximum absorbance at 260 nm. An absorbance scan of the sample is taken from 200 nm to 350 nm to enable 260/280 and 260/230 ratios to be obtained. The 260/280 ratio indicates the purity of the RNA. The 260/230 ratio indicates the level of contaminants that have absorbencies at 230 nm; including protein, phenol and chaotropic salts like guanidinium isothiocyanate. The Beer's Lambert Equation relates the absorbance of the RNA sample at 260 nm to the concentration of the RNA in the sample, thus the concentration may also be determined.

The integrity of the RNA was measured using the Agilent Bioanalyser (Agilent Technologies, CA, US). This Bioanalyser transfers the principals of gel electrophoreses to a chip format thus reducing separation time and sample consumption. The chip has sample wells, gel wells and a well for an external standard (ladder). There are micro-channels that interconnect these wells. These micro-channels become filled with a sieving polymer and fluorescence dye. The chip becomes an integrated electrical circuit when the wells and channels are filled. There are then electrodes that fit into each well, thus providing the voltage gradient that drives the movement of charged RNA molecules through the sieving polymer. The constant mass-to-charge ratio and the presence of this sieving polymer result in the RNA molecules being separated by size. As with gel electrophoresis, the smaller molecules migrate faster than larger ones.

The fluorescent dye molecules intercalate into the RNA strands such that the RNA/dye complexes may be detected by laser-induced fluorescence. The ladder contains fragments of known sizes and concentrations, the resultant fluorescence readings of which are used to plot the standard curve for migration time versus fragment size. The migration of each fragment is used to calculate fragment size. There is a marker fragment that is run with each sample to align the ladder and samples, thus normalising any drifts occurring during a run. The fluorescence readings are translated into gel-like images and electropherograms (fluorescence intensity versus migration time) for every sample. The area under the ladder is compared with the sum of sample peak areas. The ribosomal ratio of 18s to 28s, an indication of RNA integrity, is also determined here.

(iv) Microarray Data Analysis

The microarray was carried out using the Human HT-12v4 genome wide chip. The method of analysis carried out was in agreement with Burton et al, 2011, Infection and immunity, 79: 499-511. There were also additional criteria that were set to filter the data and therefore give a list of target genes;

I. The level of expression in diseased samples had to be significantly different with a significance level of p<0.05, II. The level of expression in diseased samples had to be increased by at least 1.5 fold compared to control samples, III. The genes that were differentially expressed had to exhibit this differential expression in whole tissue and fibroblasts, IV. The functionality of the genes had to be relevant to fibrosis and V. The mRNA expression profile was validated with Q-PCR data on a larger number of donor fibroblast cultures.

B—Quantitative PCR

Quantitative PCR (Q-PCR) provides a means of real time quantification of gene expression. The Q-PCR technology utilised in this thesis was TaqMan Q-PCR (Invitrogen, Paisley UK). TaqMan technology is based upon oligonucleotide probes which have a fluorophore covalently attached to the 5'-end and a quencher at the 3'-end. These probes bind to cDNA within the coding region of the gene of interest and it is only upon these oligonucleotides being degraded by DNA polymerase that the fluorescence is unmasked from the quencher.

In addition to this, the coding region itself is amplified through specific primers thus this method provides additional measures of gene specificity. Ultimately, the fluorescence detected is directly proportional to the fluorophore released and the amount of DNA template present in the PCR.

These experiments aimed to validate data obtained from the microarray. Therefore, this method was not only carried out on an increased number of donor cultures, but also with passages 4 to 6—from every culture, thus ensuring that gene expression was maintained throughout continual culture. This data would also dictate the parameters in which the cells would give optimal, robust and reproducible results for latter experiments. Experiments were performed in triplicate for 12 OcMMP patient and 4 control explant cultures (F-PemI fibroblasts, n=6; F-PemU fibroblasts, n=6; F-C fibroblasts, n=4). Human TaqMan primers for Human CD24 (Cluster of differentiation 24, Hs03044178_g1), Human SEC13 (SEC13-Like Protein 1, Hs01115007_m1), Human ALDH1A3 (Aldehyde dehydrogenase family 1 member A3, Hs00167476_m1) and Human HRPT1 (hypoxanthine phosphoribosyltransferase 1, Hs02800695_m1) genes were purchased from Applied Biosystems. HPRT1 was the endogenous control. Real-time RT-PCR18 was performed in a two-step manner.

The TaqMan experiments were carried out in 2 stages; obtaining cDNA via the eppendorf Mastercycler (Eppendorf, Hamburg, Germany) and Q-PCR via Taqman (Applied Biosystems) Due to the Q-PCR reaction amplifying cDNA, it is vital that only the cDNA (obtained from reverse transcribing template RNA) is amplified and not genomic DNA. There were two measures taken to ensure elimination of genomic DNA (gDNA). Firstly, there was enzymatic digestion of gDNA within the process of isolating template RNA and secondly, the Qiagen Quantitect reverse transcription kit (Qiagen, Hilden GER) also incorporates a further genomic DNA elimination step. The Quantitect reverse transcription step was carried out as per manufacturer's instructions for 200 ng of RNA per reaction. Briefly random hexamers (Qiagen) were used to generate cDNA from 200 ng RNA and the samples were cycled at 42° C. for 15 minutes and then at 93° C. for 3 minutes.

Each Q-PCR experiment was run as per manufacturer's instructions. TaqMan Universal PCR Master Mix (Applied Biosciences) was used in subsequent PCR reactions according to the manufacturer's protocols. Briefly each sample contained 20% cDNA (v/v), 50% Taqman Master mix (v/v), 5% Taqman Primer/Probe Mix (v/v) and 25% RNase/DNase-free water (v/v).

QPCR Data Analysis

All real-time RT-PCR experiments were performed with at least 4 experimental repeats and 3 biological repeats. The expression level of gene transcripts was standardized relative to that of HPRT1 in the same reaction using the ΔΔCT method. An overall comparison of the mean values across F-C, F-PemU and F-PemI fibroblasts was made using one-way analysis of variance.

C—Collagen Production

A competitive ELISA (MD Bioproducts, Zurich, Germany) method was used to quantify the matrix production from a monolayer of F-C, F-PemU and F-PemI fibroblasts. The competitive assay is a colormetric based immunoassay utilises a biotinylated polyclonal antibody to Collagen Type I and purified human collagen type I as an antigen. The purified human collagen is bound to the surface of the micro wells and thus competes with free collagen from samples and standards. This results in an inverse relationship between OD values and concentration: the higher the OD value, the lower the concentration of collagen type I in the sample.

Each experiment was carried out per manufacturer's instructions and performed with at least 4 experimental repeats and 3 biological repeats. The medium in which the cells were cultured for the collagen production assay was also used for the collagen secretion assay. This was in order to get an indication of the relationship between collagen production and secretion of the fibroblasts. Another method that has been noted for quantifying the level of collagen production in OcMMP fibroblasts is Q-PCR quantification of collagen type 1 mRNA expression post TGF-β induction (Razzaque et al., 2003, Investigative ophthalmology and visual science, 44: 3417-3423, 1616-1621 and 1998-2003). The ELISA utilised in our study indicates collagen type 1 protein expression and thus is superior to measuring mRNA transcripts. Scleroderma fibroblasts have also been characterised for their collagen type 1 production via ELISA.

D—Collagen Secretion

The Sircol assay (Biocolour Labs, Northern Ireland, UK) was used to assess the collagen secreted by F-C, F-PemU and F-PemI fibroblasts. The medium in which the cells were cultured for the collagen production assay was used for this Sircol collagen secretion assay. This was in order to get an indication of the relationship between collagen production and secretion of the fibroblasts. The Sircol assay was carried out according to the manufacturer's instructions on 1 ml of medium and standards. There were at least 4 experimental repeats and 3 biological repeats per Sircol assay.

The principal component of the Sircol assay is Sirius Red dye. Sirius Red binds to collagen and thus there is a linear relationship between the absorbance at 540 nm and the amount of collagen within the culture medium. Unlike the collagen type 1 ELISA, the Sircol assay method accounts for all types of collagen.

E—Measuring Aldehyde Dehydrogenase Activity

The following assay can be used to measure aldehyde dehydrogenase activity.

1. CONDITIONS: Temperature=25° C., pH=8.0, Absorption at 340 nm (A340 nm), Light path=1 cm
2. METHOD: Continuous Spectrophotometric Rate Determination
3. REAGENTS:
    A. 1 M Tris HCl Buffer, pH 8.0 at 25° C.
    B. 20 mM β-Nicotinamide Adenine Dinucleotide, Oxidized Form, Solution (β-NAD)
    C. 100 mM Acetaldehyde Solution
    D. 3 M Potassium Chloride Solution (KCl)
    E. 1 M 2-Mercaptoethanol Solution (2-ME)
    F. 100 mM Tris HCl Buffer with 0.02% (w/v) Bovine Serum Albumin, pH 8.0 at 25° C.
    G. Aldehyde Dehydrogenase Enzyme Solution
4. PROCEDURE: Pipette (in milliliters) the following reagents into suitable cuvettes:

| Component | Test | Blank |
| --- | --- | --- |
| Deionized Water | 2.32 | 2.32 |
| Reagent A | 0.30 | 0.30 |
| Reagent B | 0.10 | 0.10 |
| Reagent D | 0.10 | 0.10 |
| Reagent C | 0.05 | 0.05 |
| Reagent E | 0.03 | 0.03 |

Mix by inversion and equilibrate to 25° C. Monitor the A340 nm until constant, using a suitably thermostatted spectrophotometer. Then add:

| Component | Test | Blank |
| --- | --- | --- |
| Reagent F | 0 | 0.10 |
| Reagent G | 0.10 | 0 |

Immediately mix by inversion and record the increase in A340 nm for approximately 5 minutes. Obtain the $\Delta A_{340nm}$/minute using the maximum linear rate for both the Test and Blank.

5. CALCULATIONS:

$$\text{Units/ml enzyme} = \frac{(\Delta A_{340\,nm}/\min \text{ Test} - \Delta A_{340\,nm}/\min \text{ Blank})(3)(df)}{(6.22)(0.1)}$$

3 = Total volume (in milliliters) of assay $df$ = Dilution factor 6.22 = Millimolar extinction coefficient of $\beta$-NADH at 340 nm 0.1 = Volume (in milliliter) of enzyme used $$\text{Units/mg solid} = \frac{\text{units/ml enzyme}}{\text{mg solid/ml enzyme}}$$

$$\text{Units/mg protein} = \frac{\text{units/ml enzyme}}{\text{mg protein/ml enzyme}}$$

6. UNIT DEFINITION: One unit will oxidize 1.0 μmole of acetaldehyde to acetic acid per minute at pH 8.0 at 25° C. in the presence of β-NAD+, potassium and thiols.
7. FINAL ASSAY CONCENTRATION: In a 3.00 ml reaction mix, the final concentrations are 103 mM Tris, 0.67 mM β-nicotinamide adenine dinucleotide, 100 mM potassium chloride, 10 mM 2-mercaptoethanol, 2 mM acetaldehyde, 0.0007% (w/v) bovine serum albumin and 0.025-0.05 unit aldehyde dehydrogenase.

Example 6—In Vivo Mouse Model

Background

Topically applied ALDH inhibitors have been proposed to have anti-fibrotic activity at the ocular surface.

Aim

To investigate their anti-fibrotic activity, a mouse model (experimental immune-mediated conjunctivitis) was used to test the effect of applying disulfiram daily as eyedrops.

Methods

Figure 5:
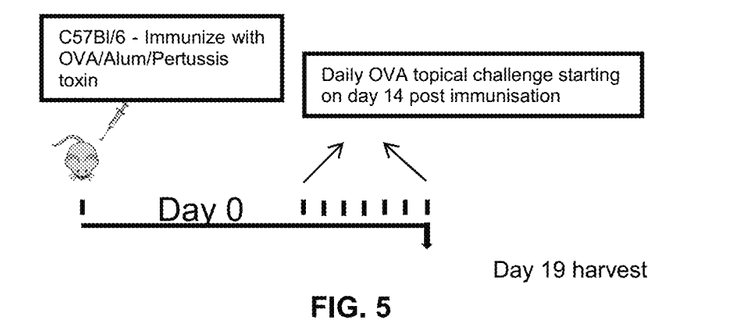
FIG. 5 shows a schematic of the mouse model used in the in vivo study as explained in more detail in Example 6.

1. The mouse model used for this study is illustrated in FIG. 5. C57Bl/6 mice, female, aged 6-8 weeks old are immunised with OVA to prime them. After 14 days, OVA is applied to the eyes (topical challenge) and after 20 minutes itching responses will be observed. After 24 hours, eyes will show early signs of conjunctival inflammation (tearing, chemosis, swelling and redness), which increases after each daily administration with OVA. A severe clinical score will usually be seen after 4-5 daily topical challenges with OVA.

In this study daily topical challenging with OVA was started on day 14 post immunisation (priming) for up to 5 days, before harvesting. See FIG. 5 for a schematic of the timepoints for OVA challenge, etc. The inflammatory scoring positively correlates with the degree of fibrosis, although it is possible that inflammation could occur in the absence of fibrosis. Therefore the clinical scores are using inflammation as a surrogate for disease.

2. To score the fibrosis, histological staining of conjunctival tissue sections was also carried out using a Trichrome staining kit for Martius, scarlet and blue, to determine the extent and localisation of the fibrotic response.

3. Dilsufiram was purchased and was solubilised in water, as per the manufacturers' recommendations. Due to its limited solubility in water, the maximum concentation possible was used.

Results

1. Potential Toxicity

Figure 6:
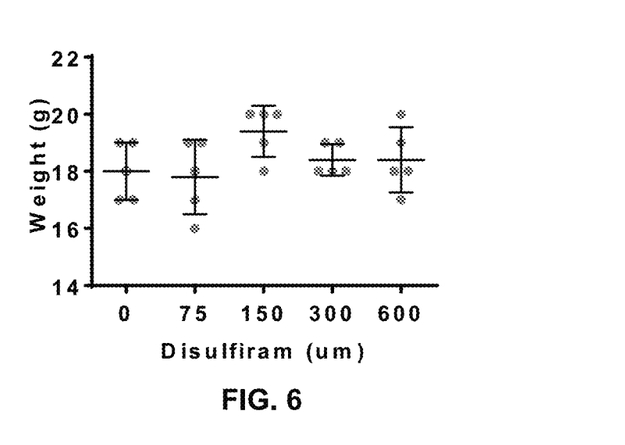
FIG. 6 shows the results from the study of potential toxicity of topically applied disulfiram to mice, as described in more detail in Example 6.

The potential toxicity of topically applied disulfiram was assessed by measuring whole body weights of naïve mice, which had not been immunised with OVA, or had received any OVA topical challenges. These naïve mice received daily disulfiram-containing eyedrops at a range of concentrations and were weighed on day 7. The results are shown in FIG. 6.

No significant change in body weight, or in any external signs of discomfort were observed throughout this treatment range. The mice labelled '0' received vehicle (i.e., water) only.

2. Inflammatory Scores

Cumulative clinical scores were measured for tearing, redness and lid swelling every 2 days for up to 6 days of daily eyedrops given one hour before daily OVA challenges. There were 5 mice per treatment group, eyedrops were given in both eyes, and scores were taken from each eye, from each mouse. The results are shown in FIG. 7.

Mean+/−SD are shown for each treatment at each time-point, and T-tests were use to assess statistical significance. The * is where $P<0.05$, and ** $P<0.01$.

Figure 7:
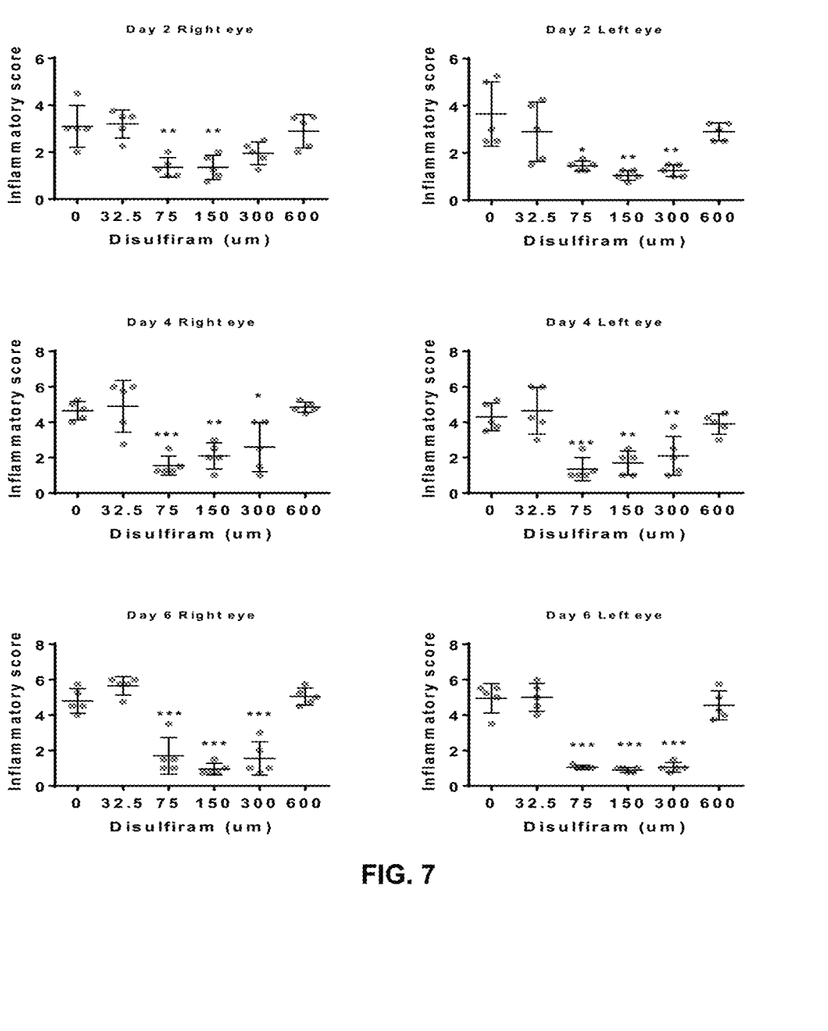
FIG. 7 shows cumulative clinical score results for inflammation in mice tested using the in vivo mouse model, as described in more detail in Example 6. The left column of graphs relates to the results in the right eyes of the subjects and the right column of graphs relates to the results in the left eyes of the subjects. The top two graphs show results after two days of daily eyedrops, the middle two graphs after four days, and the bottom two graphs after six days. Mean+/−SD are shown as vertical bars for each treatment at each timepoint. T-tests were used to assess statistical significance: the * is where $P<0.05$ and ** $P<0.01$.

As can be seen in FIG. 7, maximum clinical scores were 5 at day 2 of OVA challenge, and were maximum in the vehicle controls, but were significantly decreased in both eyes in response to increasing concentrations of disulfiram, except at the highest concentration used (600 μM). This was thought to be due to a toxicity at this highest concentration and was confirmed by the histology results. At this highest concentration, although increased clinical scores were detected, this was not reflected in an increase in fibrosis in the tissues. That observation would suggest that the increased inflammation at 600 μM reflected a non-specific inflammation due to a toxicity at the ocular surface due to the disulfiram.

3. Fibrosis

Figure 8:
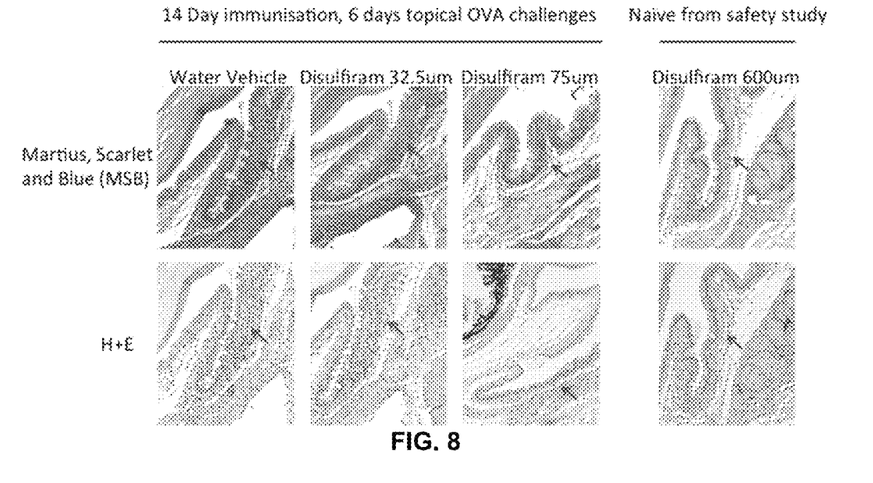
FIG. 8 shows histological results obtained as described in more detail in Example 6. Conjunctival tissue sections were stained to identify the fibrotic response in the tissues, which typically occurs beneath the epithelium, and as shown in the arrows.

Conjunctival tissue sections were stained to identify the fibrotic response in the tissues, which typically occurs beneath the epithelium, and is shown in the arrows of FIG. 8. In comparison with the vehicle control, there was a marked decrease in the degree of fibrosis at the 75 uM concentrations of disulfiram. The histology from naïve mice receiving disulfiram eyedrops demonstrated that, at the maximum concentration, there was no evidence of toxicity.

CONCLUSIONS

These in vivo studies involved immunisation of naïve mice with a model antigen (OVA) followed, at 14 days, by daily challenges with the same OVA to the ocular surface.

Given that 5-7 daily challenges with OVA also results in detectable levels of fibrosis, this model was used to investigate the potential anti-fibrotic effects of disulfiram.

In this study, water was selected as a vehicle for solubilising the compound.

Whilst the clinical scoring was used as a readout of inflammation, there is a good correlation with the degree of fibrosis. However, the highest concentration of disulfiram used in the study upregulated inflammation, but not fibrosis. With this in mind, it is noted that the fibrosis response can be confirmed by histological staining.

In conclusion, dilsufiram significantly decreased both the inflammatory response and the fibrosis when administered topically to the eye.

The invention claimed is:

1. A method for treating or preventing mucous membrane pemphigoid (MMP) in a patient in need thereof, the method comprising administering to said patient an aldehyde dehydrogenase inhibitor, wherein the aldehyde dehydrogenase inhibitor is tetraethylthioperoxydicarbonic diamide (disulfiram) or 4-(diethylamino)benzaldehyde (DEAB).

2. The method according to claim 1, wherein the aldehyde dehydrogenase inhibitor is tetraethylthioperoxydicarbonic diamide (disulfiram).

3. The method according to claim 1, wherein the aldehyde dehydrogenase inhibitor is 4-(diethylamino)benzaldehyde (DEAB).

4. The method according to claim 1, wherein the fibrosis is ocular mucous membrane pemphigoid (OcMMP).

* * * * *